US010251678B2

(12) United States Patent
Alsup et al.

(10) Patent No.: US 10,251,678 B2
(45) Date of Patent: Apr. 9, 2019

(54) ROD CONNECTOR WITH SWIVEL COLLET

(71) Applicants: Jeremy Stevan Alsup, Bountiful, UT (US); Justin Burnell Hohl, Sandy, UT (US)

(72) Inventors: Jeremy Stevan Alsup, Bountiful, UT (US); Justin Burnell Hohl, Sandy, UT (US)

( * ) Notice: Subject to any disclaimer, the term of this patent is extended or adjusted under 35 U.S.C. 154(b) by 20 days.

(21) Appl. No.: 15/352,577

(22) Filed: Nov. 15, 2016

(65) Prior Publication Data

US 2017/0128107 A1    May 11, 2017

Related U.S. Application Data

(63) Continuation of application No. 14/572,408, filed on Dec. 16, 2014, now Pat. No. 9,492,205.

(51) Int. Cl.
*A61B 17/70*     (2006.01)
*A61B 17/86*     (2006.01)

(52) U.S. Cl.
CPC .......... *A61B 17/7052* (2013.01); *A61B 17/70* (2013.01); *A61B 17/705* (2013.01); *A61B 17/7049* (2013.01); *A61B 17/86* (2013.01)

(58) Field of Classification Search
CPC .................................................. A61B 17/705
See application file for complete search history.

(56) References Cited

U.S. PATENT DOCUMENTS

| | | | | |
|---|---|---|---|---|
| 8,998,961 B1* | 4/2015 | Ziemek | .................. | A61B 17/86 606/260 |
| 9,492,205 B2* | 11/2016 | Alsup | ................ | A61B 17/7049 |
| 2005/0261687 A1* | 11/2005 | Garamszegi | ....... | A61B 17/7011 606/305 |
| 2007/0270817 A1* | 11/2007 | Rezach | .............. | A61B 17/7049 606/252 |
| 2008/0103507 A1* | 5/2008 | Purcell | ............... | A61B 17/7052 606/103 |
| 2009/0270924 A1* | 10/2009 | Wing | ................. | A61B 17/7011 606/280 |
| 2014/0100613 A1* | 4/2014 | Iott | .................... | A61B 17/7074 606/279 |
| 2014/0277137 A1* | 9/2014 | Stad | ................... | A61B 17/7076 606/246 |
| 2014/0277155 A1* | 9/2014 | Barrus | ............... | A61B 17/7056 606/276 |

* cited by examiner

*Primary Examiner* — Nicholas J Plionis
(74) *Attorney, Agent, or Firm* — James M. Smedley LLC; James Michael Smedley, Esq.

(57) ABSTRACT

The present invention generally relates to a rod connector for adding a pedicle rod to an existing spinal fusion construct. Specifically, this invention relates to an open rod connector that has a swiveling rod collet that allows for a pedicle rod to be rotated into the desired alignment.

20 Claims, 5 Drawing Sheets

ROD CONNECTOR WITH SWIVEL COLLET

CROSS-REFERENCE TO RELATED APPLICATIONS

This application is a continuation-in-part of U.S. Non-Provisional application Ser. No. 14/572,408, filed on Dec. 16, 2014 and entitled "Rod Connector with Swivel Collet the entire disclosure of which is hereby incorporated herein by reference.

FIELD OF THE INVENTION

The present invention generally relates to a rod connector for adding a pedicle rod to an existing spinal fusion construct. Specifically, this invention relates to an open rod connector that has a swiveling rod collet that allows for a pedicle rod to be rotated into the desired alignment.

BACKGROUND OF THE INVENTION

A rod connector is a hardware article that is frequently used in spinal fusion surgery. In particular, a rod connector allows for the addition of a new pedicle rod to a spinal fusion construct. Moreover, rod connectors allow for the extension of an existing final fusion construct, without the need to remove the existing fusion construct and start from new. Currently existing rod connectors, however, can be difficult to connect and align with an existing construct. In particular, existing rod connectors do not provide for any degree of rotation so that the new pedicle rod that is being added to the fusion construct can be easily aligned with the existing pedicle rod. This can lead to situations where either the new pedicle rod is not connected to the existing fusion construct in an ideal alignment or where existing portions of the fusion construct have to be removed to ensure proper alignment over the entire length of the construct.

Therefore, there is a need in the art for a rod connector that is configured to allow a pedicle rod to rotate within a rod connector so that a new pedicle rod can be properly aligned with a pedicle rod of an existing fusion construct. These and other features and advantages of the present invention will be explained and will become obvious to one skilled in the art through the summary of the invention that follows.

SUMMARY OF THE INVENTION

Accordingly, embodiments of the present invention are directed to providing a rod connector with swiveling collet. Embodiments of the present invention may include a rod connector with at least one channel with a rotating collet that allows a pedicle rod to be swiveled into a desired position.

According to an embodiment of the present invention, an open rod connector for adding a pedicle rod to an existing fusion construct, the open rod connector comprising: a connector body formed with a first rod connector channel defined by a side wall and a middle wall and a second rod connector channel defined by the middle wall and a shaped arm, wherein the first rod connector channel is comprised of an upper portion formed with internal threading and a lower portion that defines a collet-receiving depression formed in a bottom surface of the first rod connector channel and the second rod connector channel that is adapted to receive a first spinal fusion rod, and a swivel collet comprised of side extensions that define a rod coupling groove adapted to receive a second spinal fusion rod and a round base that rotates within the collet-receiving depression of the first rod connector channel.

According to an embodiment of the present invention, the open rod connector is further comprised of a collet pin that engages with a collet pin outlet formed in the side wall of the connector body and a collet pin slot formed in one of the side extensions of the swivel collet, wherein the collet pin engages with the collet pin slot via the collet pin outlet to limit rotation of the swivel collet.

According to an embodiment of the present invention, the internal threading of the upper portion of the first rod connector channel is configured to receive a set screw.

According to an embodiment of the present invention, the first rod connector channel is formed as a U-shaped channel configured to connect from beneath the second spinal fusion rod.

According to an embodiment of the present invention, the first side wall, the middle wall, and the shaped arm extend vertically from a base portion of the connector body such that the first rod connector channel and the second rod connector channel are both open at a top portion of the connector body that is opposite of the base portion.

According to an embodiment of the present invention, the second rod connector channel is formed as a U-shaped channel that is configured to connect from beneath the first spinal fusion rod and is comprised of an upper portion formed with internal threading and a lower portion that is adapted to receive the first spinal fusion rod.

According to an embodiment of the present invention, the internal threading of the upper portion of the second rod connector channel is configured to receive a set screw.

According to an embodiment of the present invention, the first side wall and the middle wall extend vertically from a base portion of the connector body and the shaped arm extends perpendicularly from the middle wall such that the first rod connector channel is open to a top portion of the body connector and the second rod connector channel is open to the base portion of the body connector.

According to an embodiment of the present invention, the second rod connector channel is formed as a C-shaped hook connector that is configured to connect over top of the first spinal fusion rod and is comprised of a hooked upper portion formed by the shaped arm of the connector body that defines a first boundary of the second rod connector channel and a lower extension lip that defines a second boundary of the second rod connector channel.

According to an embodiment of the present invention, the hooked upper portion is formed with a threaded screw hole.

According to an embodiment of the present invention, the open rod connector comprising: a connector body formed with a first side wall, a middle wall, and a second side wall each of which extend vertically from a base portion of the connector body to form a top portion and a top surface of the connector body, a first rod connector channel defined by the first side wall and a first edge of the middle wall, wherein the first rod connector channel is comprised of an upper portion that is formed with internal threading and a lower portion that defines a collet-receiving depression formed in a bottom surface of the first rod connector channel, a second rod connector channel defined by the second side wall and a second edge of the middle wall, wherein the second rod connector channel is comprised of an upper portion that is formed with internal threading and a lower portion that is adapted to receive a first spinal fusion rod, wherein the first rod connector channel and the second rod connector channel are open at the top surface of the connector body, and a swivel collet comprised of side extensions that define a rod coupling groove adapted to receive a second spinal fusion rod and a round base that rotates within the collet-receiving depression of the first rod connector channel.

According to an embodiment of the present invention, the first rod connector channel and the second rod connector channel are U-shaped.

According to an embodiment of the present invention, the internal threading of the upper portions of the first and second rod connector channels are configured to receive a set screw.

According to an embodiment of the present invention, an open rod connector for adding a pedicle rod to an existing fusion construct, the open rod connector comprising: a connector body formed with a side wall, a middle wall, and a shaped arm, wherein the side wall and the middle wall extend vertically from a base portion of the connector body to form a top portion of the connector body and the shaped arm extends perpendicularly from the middle wall, a first rod connector channel defined by the first side wall and a first edge of the middle wall, wherein the first rod connector channel is comprised of an upper portion that is formed with internal threading and a lower portion that defines a collet-receiving depression formed in a bottom surface of the first rod connector channel, a second rod connector channel defined by the shaped arm, a second edge of the middle wall, and a lower extension lip extending from the second edge of the middle wall at the base portion of the connector body, wherein the extension arm is formed with a threaded screw hole, wherein the first rod connector channel is open to the top portion of the body connector and the second rod connector channel is open to the base portion of the body connector, and a swivel collet comprised of side extensions that define a rod coupling groove adapted to receive a first spinal fusion rod and a round base that rotates within the collet-receiving depression of the first rod connector channel.

According to an embodiment of the present invention, the first rod connector channel is U-shaped and the second rod connector channel is C-shaped.

According to an embodiment of the present invention, the second rod connector channel is formed as a C-shaped hook connector that is configured to connect over top of a second spinal fusion rod and is comprised of a hooked upper portion formed by the shaped arm of the connector body that defines a first boundary of the second rod connector channel and the lower extension lip that defines a second boundary of the second rod connector channel.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

DETAILED SPECIFICATION

The present invention generally relates to a rod connector for adding a pedicle rod to an existing spinal fusion construct. Specifically, this invention relates to an open rod connector that has a swiveling rod collet that allows for a pedicle rod to be rotated into the desired alignment.

According to an embodiment of the present invention, an open rod connector is comprised of a connector body, a swivel collet, and a collet pin. Additional components may include set screws to secure a pedicle rod in the rod connector channels that are formed in the connector body. Some embodiments of the present invention may include fewer or additional components depending on the specific application of the open rod connector. One of ordinary skill in the art would appreciate that there are many possible configurations and components for an open rod connector, and embodiments of the present invention are contemplated for use with any such configuration or component.

According to an embodiment of the present invention, the open rod connector is constructed from a variety of durable materials. In a preferred embodiment, the majority of the open rod connector is comprised of any variety of metal or metal alloy suitable for use inside the human body. An example of a suitable metal includes, but is not limited to, Titanium 6Al-4V ELI. One of ordinary skill in the art would appreciate that there are numerous suitable materials from which the components of the open rod connector could be manufactured, and embodiments of the present invention are contemplated for use with any such material.

According to an embodiment of the present invention, the open rod connector is comprised of a connector body. In a preferred embodiment, the connector body is formed with a first rod connector channel and second rod connector channel. In some embodiments, the connector body may also be formed with a collet pin outlet. In a first preferred embodiment, the connector body is a dual tulip open rod connector. In an alternate preferred embodiment, the rod connector body is a hooked open rod connector. In alternate embodiments, the connector body may be formed with more than two rod connector channels. In other alternate embodiments, the connector body may be formed with only one rod connector channel. One of ordinary skill in the art would appreciate that there are many suitable designs for a connector body, and embodiments of the present invention are contemplated for use with any such design.

According to an embodiment of the present invention, the connector body is a dual tulip open rod connector. In a preferred embodiment, the dual tulip open rod connector (or dual tulip connector) is formed with a first rod connector channel and a second rod connector channel. The dual tulip open rod connector may also be formed with a collet pin outlet. In the preferred embodiment, the dual tulip connector is comprised of a first side wall, a middle wall, and a second side wall, each of which extend vertically from a base portion of the dual tulip connector. The tops of each of the first side wall, middle wall, and second side wall, form the top portion of the dual tulip connector, with the outer surface of the top portion being the top surface of the dual tulip connector. In the preferred embodiment, the collet pin outlet is formed at the bottom, center portion of the first side wall. One of ordinary skill in the art would appreciate that there are many possible configurations for a dual tulip open rod connector, and embodiments of the present invention are contemplated for use with any such configuration.

According to an embodiment of the present invention, the dual tulip connector is formed with a first and second rod connector channel. In a preferred embodiment, the first rod connector channel is defined by the first side wall and a first edge of the middle wall, while the second rod connector channel is defined by the second side wall and a second edge of the middle wall. In the preferred embodiment of the dual tulip connector both the first and second rod connector channel open to the top surface of the dual tulip connector. In the preferred embodiment, each of the rod connector channels may be generally U-shaped. In other embodiments, the rod connector channels may be formed with any shape that is suitable for receiving a pedicle rod of a spinal fusion construct. In the preferred embodiment, the upper portion of each of the rod connector channels is configured with threading on the upper inner surface of the channel. This threading is designed to receive a set screw or other fastening means for holding the pedicle rod in place with the rod connector channel. In a preferred embodiment, the lower portion of the first rod connector defines a collet-receiving depression that is formed in the bottom surface of the first rod connector channel. The collet-receiving depression is adapted to receive the swivel collet and allow the swivel collet to rotate within the collet-receiving depression. One of ordinary skill in the art would appreciate that there are numerous possible designs for each of the rod connector channels, and embodiments of the present invention are contemplated for use with any such design.

According to an embodiment of the present invention, the connector body is a hooked open rod connector. In a preferred embodiment, the hooked open rod connector (or hooked connector) is formed with a first rod connector channel and a second rod connector channel. The hooked open rod connector may also be formed with a collet pin outlet. In the preferred embodiment, the hooked connector is comprised of a side wall, a middle wall, and a shaped arm. In the preferred embodiment the side wall and the middle wall extend vertically from a base portion of the hooked connector, while the shaped arm extends perpendicularly from the middle wall in the opposite direction of the first rod connector channel. The tops of each of the side wall, middle wall, and shaped arm, form the top portion of the hooked connector, with the outer surface of the top portion being the top surface of the hooked connector. In some embodiments, the extension arm is narrower relative to the width of the side and middle walls. In the preferred embodiment, the collet pin outlet is formed at the bottom, center portion of the side wall. One of ordinary skill in the art would appreciate that there are many possible configurations for a hooked open rod connector, and embodiments of the present invention are contemplated for use with any such configuration.

According to an embodiment of the present invention, the hooked connector is formed with a first and second rod connector channel. In a preferred embodiment, the first rod connector channel is defined by the side wall and a first edge of the middle wall, while the second rod connector channel is defined by the shaped armed extending from a second edge of the middle wall, the second edge of the middle wall, and a lower extension lip extending from the bottom of the second edge of the middle wall. In the preferred embodiment of the hooked connector, the first connector channel opens to the top surface of the hooked connector, while the second rod connector channel opens to the base portion of the hooked connector. In the preferred embodiment, the first rod connector channel is generally U-shaped, while the second rod connector channel is generally C-shaped. In other embodiments, the rod connector channels may be formed with any shape that is suitable for receiving a pedicle rod of a spinal fusion construct. In the preferred embodiment, the upper portion of the first rod connector channel is configured with threading on the upper inner surface of the channel. This threading is designed to receive a set screw or other fastening means for holding the pedicle rod in place with the rod connector channel. In the preferred embodiment, the lower portion of the first rod connector defines a collet-receiving depression that is formed in the bottom surface of the first rod connector channel. The collet-receiving depression is adapted to receive the swivel collet and allow the swivel collet to rotate within the collet-receiving depression. In the preferred embodiment, the second rod connector channel is formed with a threaded screw hole in the top of the shaped arm. One of ordinary skill in the art would appreciate that there are numerous possible designs for each of the rod connector channels, and embodiments of the present invention are contemplated for use with any such design.

According to an embodiment of the present invention, the connector body is formed with a first rod connector channel. In a preferred embodiment, the first rod connector channel is a U-shaped channel that is defined by a side wall and a middle wall that extends from the base of the connector body. In the preferred embodiment, the first rod connector channel is comprised of an internally threaded upper portion, a collet pin outlet, and a lower portion that defines a collet-receiving depression formed in the bottom surface of the first rod connector channel. The collet pin outlet is formed in the bottom, center side wall of the connector body. The collet-receiving depression is configured to receive the swivel collet and to allow the swivel collet to rotate within the collet-receiving depression. In the preferred embodiment, the first rod connector channel connects to a pedicle rod from beneath the pedicle rod. In some embodiments, the connector body is further formed with an angled surface edge portion at the boundary formed between the side edges of the first rod connector channel and the edges of each of the side and middle walls. In the preferred embodiment, the angled surface edge portion allows a pedicle rod that is being held by the swivel collet to rotate with greater freedom than if a 90 degree angle was formed between the first rod connector channel and edges of the side and middle walls. The angle of the angled surface edge portion (along with the configuration of the collet pin slot, as discussed below) impacts the degree of rotation the pedicle rod can achieve, with wider angles allowing for a greater degree of rotation. One of ordinary skill in the art would appreciate that there are many suitable designs for a first rod connector channel and embodiments of the present invention are contemplated for use with any such design.

According to an embodiment of the present invention, the connector body is formed with a second rod connector channel. In a first preferred embodiment, the second rod connector channel is a U-shaped channel that is defined by a side wall and a middle wall that extend from the base of the connector body. In the first preferred embodiment, the second rod connector channel is comprised of an internally threaded upper portion and a lower portion that is adapted to receive a pedicle rod. In the first preferred embodiment, the second rod connector channel connects to a pedicle rod from beneath the pedicle rod. In a second preferred embodiment, the second rod connector channel is a C-shaped channel that is defined by a shaped arm extending from the top of the middle wall of the connector body, a curved portion of the middle wall, and a lower extension lip extending from the bottom of the middle wall. In the second preferred embodiment, the second rod connector channel is comprised of a hooked upper portion that is substantially formed by the shaped arm and a threaded screw hole formed in the hooked upper portion. The tip of the hooked upper portion defines the first boundary of the C-shaped channel and the tip of the lower extension lip defines the second boundary of the C-shaped channel. In the second preferred embodiment, the second rod connector channel connects over top of the pedicle rod. One of ordinary skill in the art would appreciate that there are many suitable designs for a second rod connector channel and embodiments of the present invention are contemplated for use with any such design.

According to an embodiment of the present invention, the connector body is formed with a collet pin outlet. In a preferred embodiment, the collet pin outlet is formed in a side wall of the connector body. In the preferred embodiment, the collet pin outlet is adapted to receive a collet pin that engages with the swivel collet to limit the rotation of the swivel collet within the collet-receiving depression of the first rod connector channel. In embodiments that include a collet pin outlet, the collet pin outlet will typically be formed in the side wall of the rod connector channel that houses the swivel collet. In the preferred embodiment, the collet pin outlet will be located in the lower, center portion of the side wall. In other embodiments, the collet pin outlet may be located in any portion of the connector body so that it may permit the collet pin to engage with the swivel collet. One of ordinary skill in the art would appreciate that there are many locations on the connector body where the collet pin outlet could be formed, and embodiments of the present invention are contemplated for use with any such collet pin outlet location.

According to an embodiment of the present invention, the open rod connector is comprised of a swivel collet. In a preferred embodiment, the swivel collet may be comprised of a round base and a pair of side extensions that define a rod coupling groove. In some embodiments, the swivel collet may be further comprised of a collet pin slot. In the preferred embodiment, the round base of the swivel collet is adapted to fit into and rotate within the collet-receiving depression formed in the first rod connector channel of the connector body, while the rod coupling groove is adapted to engage with a pedicle rod of a spinal fusion construct. The rod coupling groove is preferably a U-shaped groove that receives the pedicle rod. In the preferred embodiment, the shape of the rod coupling groove correlates to the shape of the first rod connector channel that houses the swivel collet and the shape of the pedicle rod. One of ordinary skill in the art would appreciate that there are many suitable configurations for a swivel collet, and embodiments of the present invention are contemplated for use with any such configuration.

According to an embodiment of the present invention, the swivel collet is comprised of a collet pin slot. In a preferred embodiment, the collet pin slot is formed in one of the side extensions of the swivel collet. In the preferred embodiment, the collet pin slot is adapted to engage with the collet pin to limit the rotation of the swivel collet. It may be beneficial to limit the rotation of the swivel collet so that the swivel collet remains properly aligned within the rod connector channel. In a preferred embodiment, the rotation of the swivel collet is limited to thirty degrees of rotation from center in either direction, for a total of sixty degrees of rotation. The length of the collet pin slot relative to the circumference of the base of the swivel collet determines the rotational limits of the swivel collet. For example, the longer the length of the collet pin slot the greater degree of rotation the swivel collet will have within the collet-receiving depression. In addition to the length of the collet pin slot, the angle of the angled surface edge portion contributes to the degree of rotation the pedicle rod can achieve, with a wider angled cut on the angled surface edge portion allowing for a greater degree of rotation. In the preferred embodiment, the collet pin engages with the collet pin slot via the collet pin outlet formed in a side wall of the connector body. One of ordinary skill in the art would appreciate that there are many suitable configurations for a collet pin slot, and embodiments of the present invention are contemplated for use with any such configurations.

According to an embodiment of the present invention, the open rod connector is comprised of a collet pin. In a preferred embodiment, the collet pin is a peg, stud, or pin-like article that is inserted into the collet pin outlet on a side wall of the connector body. In the preferred embodiment, the collet pin functions to limit the rotation of the swivel collet by engaging with the collet pin slot on the swivel collet. In the preferred embodiment, the collet pin is comprised of a round head portion and shaft portion with a rounded tip, where the shaft portion is smaller in circumference than the head portion. The shaft portion of the collet pin is inserted into the collet pin outlet on the connector body and the head portion of the collet pin functions as a stop to prevent the collet pin being pushed entirely through the collet pin outlet. One of ordinary skill in the art would appreciate that there are many suitable designs for a collet pin, and embodiments of the present invention are contemplated for use with any such configurations.

According to an embodiment of the present invention, the open rod connector is comprised of a plurality of set screws. In a preferred embodiment, the set screws are designed to secure a pedicle rod in place within the rod connector channels of the connector body. In a dual tulip connector embodiment of the present invention, the set screws are fastened to the connector body via the internal threading on the upper portions of each of the first and second rod connector channels. In a hooked connector embodiment of the present invention, the set screws are attached to the internal threading on the upper portion of the first rod connector channel and to the screw hole formed in the hooked upper portion of the second rod connector channel. One of ordinary skill in the art would appreciate that there are many fasteners that could be used in place of a set screw, and embodiments of the present invention are contemplated for use with any such fastener.

Exemplary Embodiments

Figure 1:
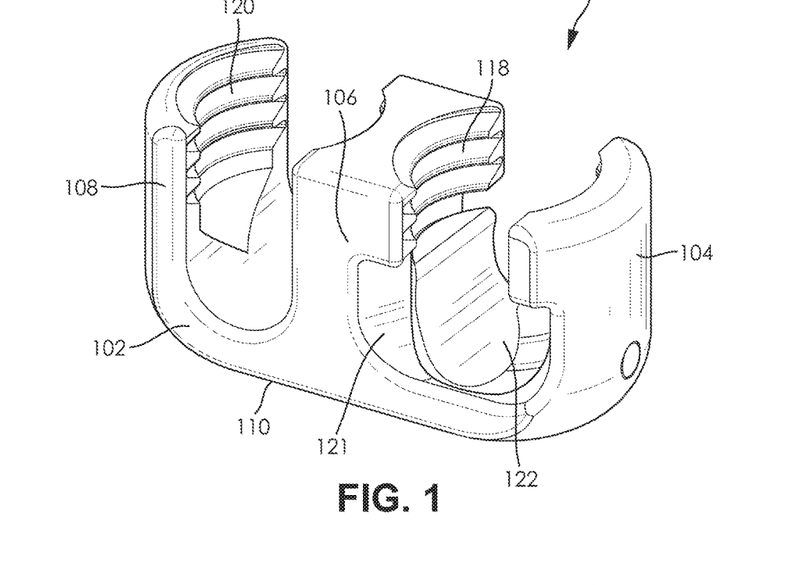
FIG. 1 is a perspective view of a dual tulip open rod connector in accordance with an embodiment of the present invention.

Turning now to FIG. 1, a perspective view of a dual tulip open rod connector in accordance with an embodiment of the present invention. In a preferred embodiment, the open rod connector 100 is comprised of a connector body 102, a swivel collet 122, and a collet pin (not shown). A first side wall 104, a middle wall 106, and a second side wall 108 extend vertically from a base portion 110 of the connector body 102 to form a first and second rod connector channel. In the preferred embodiment, the swivel collet 122 is retained in the first rod connector channel. Furthermore, the first rod connector channel and the second rod connector channel each include internal threading 118, 120 at the top portion of each of the channels. In the preferred embodiment, the width of the top of the connector body 102 is approximately 11 millimeters, while the distance between the centers of the first and second rod connector channels is approximately 12.5 millimeters. Furthermore, in the preferred embodiment, the swivel collet 122 may be rotated approximately thirty degrees from center in either direction, for a total of sixty degrees of rotation. In some embodiments, the connector body 102 may also be formed with an angled surface edge portion 121 at the edges of the first side wall 104 and middle wall 106 that border the first rod connector channel 114. In the preferred embodiment, the angled surface edge portion 121 may limit the rotation of a pedicle rod (not shown) and therefore limit indirectly the rotation of the swivel collet 122 when the swivel collet 122 is holding a pedicle rod (not shown). One of ordinary skill in the art would appreciate that any of the above ranges and measurements could be increased or decreased based upon the design and application of the open rod connector.

Figure 2:
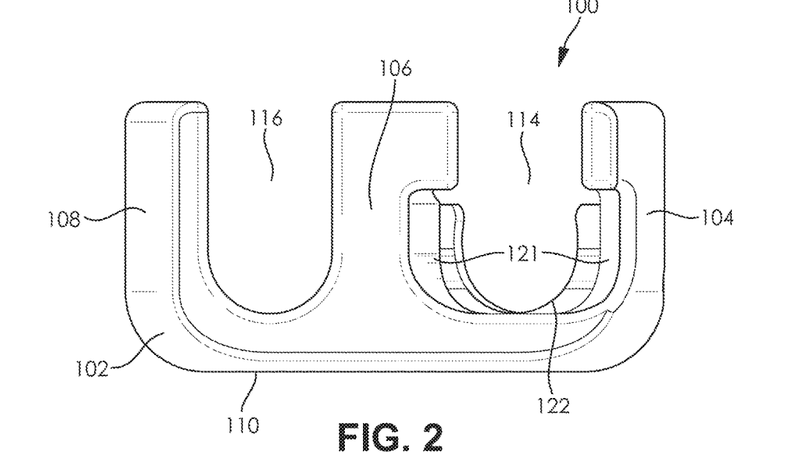
FIG. 2 is a front view of a dual tulip open rod connector in accordance with an embodiment of the present invention.

Turning now to FIG. 2, a front view of a dual tulip open rod connector in accordance with an embodiment of the present invention. In a preferred embodiment, the open rod connector 100 is comprised of a connector body 102, a swivel collet 122, and a collet pin (not shown). A first side wall 104, middle wall 106, and second side wall 108 extend vertically from a base portion 110 of the connector body 102 to form a first rod connector channel 114 and a second rod connector channel 116. In the preferred embodiment, the swivel collet 122 is retained in the first rod connector channel 114. In some embodiments, the connector body 102 may also be formed with an angled surface edge portion 121 at the edges of the first side wall 104 and middle wall 106 that border the first rod connector channel 114.

Figure 3:
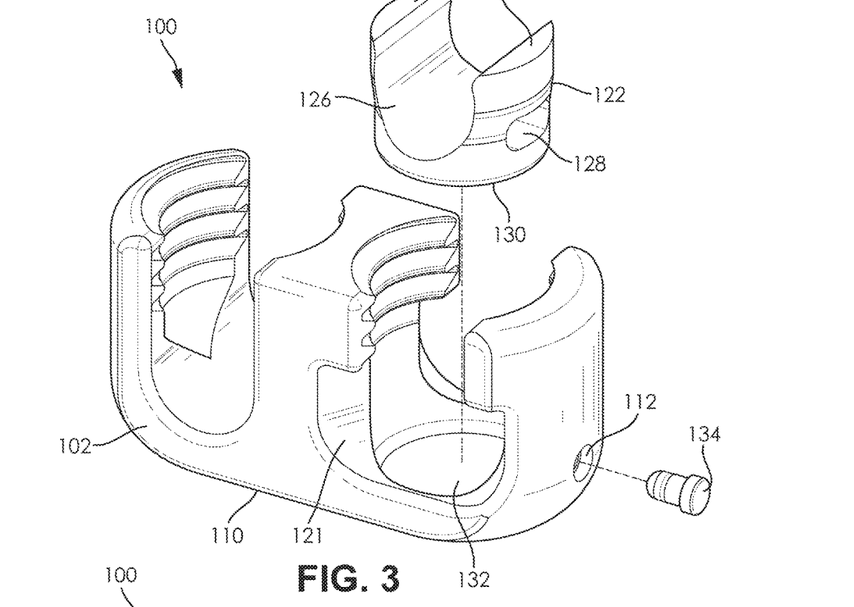
FIG. 3 is an exploded view of a dual tulip open rod connector in accordance with an embodiment of the present invention.

FIG. 3 is an exploded view of a dual tulip open rod connector in accordance with an embodiment of the present invention. In a preferred embodiment, the open rod connector 100 is comprised of a connector body 102, a swivel collet 122, and a collet pin 134. A first side wall, middle wall, and second side wall extend vertically from a base portion 110 of the connector body 102 to form a first and second rod connector channel. In the preferred embodiment, the swivel collet 122 is retained in a collet-receiving depression 132 formed in the first rod connector channel. The swivel collet 122 is comprised of a round base 130 and two side extensions 124 that define a rod coupling groove 126. The swivel collet 122 may also be formed with a collet pin slot 128. The collet pin 134 is inserted into the connector body 102 at a collet pin outlet 112 formed in the first side wall of the connector body 102. In some embodiments, the connector body 102 may also be formed with an angled surface edge portion 121 at the edges of the first side wall and second side wall that border the first rod connector channel.

Figure 4:
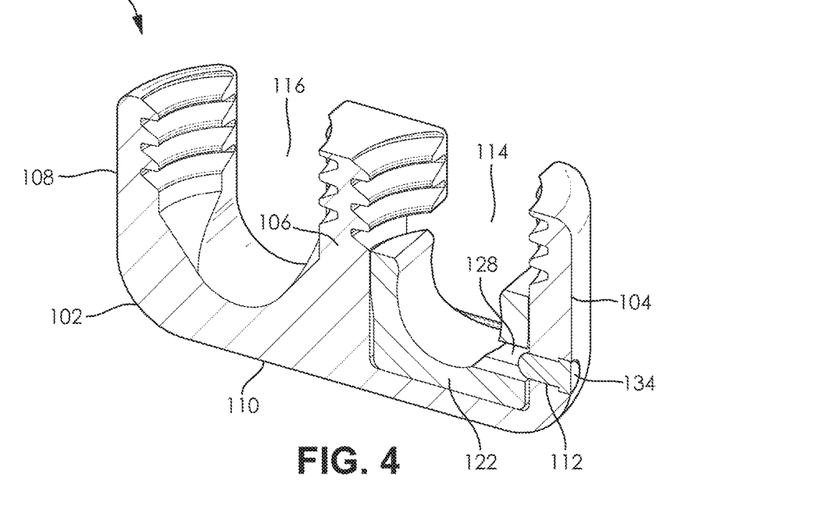
FIG. 4 is a cross-sectional view of a dual tulip open rod connector in accordance with an embodiment of the present invention.

FIG. 4 is a cross-sectional view of a dual tulip open rod connector in accordance with an embodiment of the present invention. In a preferred embodiment, the open rod connector 100 is comprised of a connector body 102, a swivel collet 122, and collet pin 134. A first side wall 104, a middle wall 106, and a second side wall 108 extend vertically from a base portion 110 of the connector body 102 to form a first rod connector channel 114 and a second rod connector channel 116. In the preferred embodiment, the swivel collet 122 is retained in a collet-receiving depression formed in the first rod connector channel 114. The swivel collet 122 may be formed with a collet pin slot 128 that engages with the collet pin 134. The collet pin 134 is inserted into the connector body 102 at a collet pin outlet 112 formed in the first side wall 104 of the connector body 102.

Figure 5:
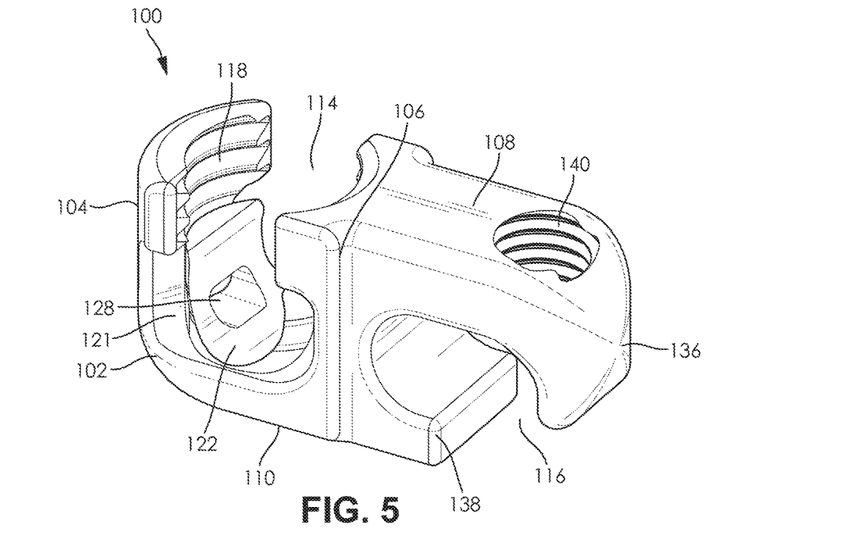
FIG. 5 is a perspective view of a hooked open rod connector in accordance with an embodiment of the present invention.

FIG. 5 is a perspective view of a hooked open rod connector in accordance with an embodiment of the present invention. In a preferred embodiment, the open rod connector 100 is comprised of a connector body 102, a swivel collet 122, and a collet pin (not shown). A side wall 104 and a middle wall 106 extend vertically from a base portion 110 of the connector body 102 to define a first rod connector channel 114, while a shaped arm 108 and a lower extension lip 138 extend perpendicularly from the middle wall 106 to define a second rod connector channel 116. In the preferred embodiment, the boundaries of the second rod connector channel 116 are defined by a hooked portion 136 of the shaped arm 108 and the lower extension lip 138. The second rod connector channel may also be formed with a threaded screw hole 140 that is formed in the shaped arm 108. Finally, the portion of the connector body 102 forming the shaped arm 108 and lower extension lip 138 may be narrower in width than the portion of the connector body 102 that forms the side wall 104 and the middle wall 106 of the connector body. In the preferred embodiment, the swivel collet 122 is retained in the first rod connector channel 114. Furthermore, the first rod connector channel 114 includes internal threading 118 at the top portion of the channel. In this view, the collet pin slot 128 formed in the swivel collet 122 can be seen. In the preferred embodiment, the width of the top of the connector body 102 is approximately 11 millimeters at the side wall 104 and steps down to a width of approximately 9 millimeters at the shaped arm 108. The distance between the centers of the first and second rod connector channels is approximately 11.5 millimeters. Furthermore, in the preferred embodiment, the swivel collet 122 may be rotated approximately thirty degrees from center in either direction, for a total of sixty degrees of rotation. In some embodiments, the connector body 102 may also be formed with an angled surface edge portion 121 at the edges of the first side wall 104 and middle wall 106 that border the first rod connector channel 114. In the preferred embodiment, the angled surface edge portion 121 may limit the rotation of a pedicle rod (not shown) and therefore indirectly limit the rotation of the swivel collet 122 when the swivel collet 122 is holding a pedicle rod (not shown). One of ordinary skill in the art would appreciate that any of the above ranges and measurements could be increased or decreased based upon the design and application of the open rod connector.

Figure 6:
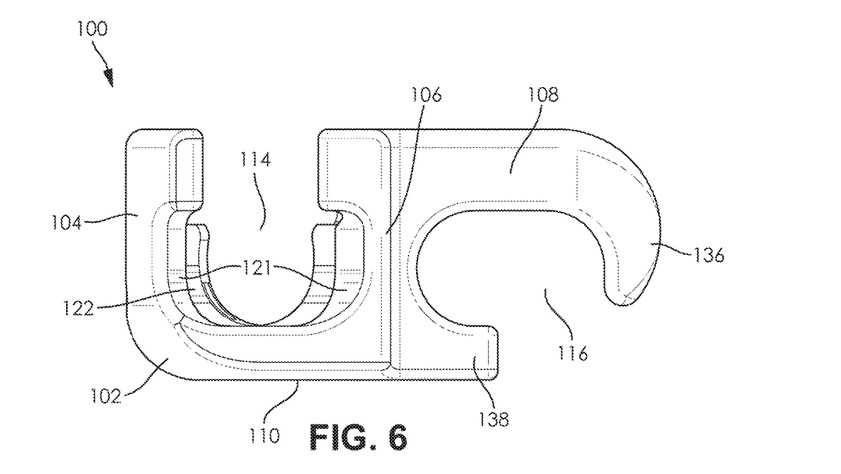
FIG. 6 is a front view of a hooked open rod connector in accordance with an embodiment of the present invention.

FIG. 6 is a front view of a hooked open rod connector in accordance with an embodiment of the present invention. In a preferred embodiment, the open rod connector 100 is comprised of a connector body 102, a swivel collet 122, and a collet pin (not shown). A side wall 104 and a middle wall 106 extend vertically from a base portion 110 of the connector body 102 to define a first rod connector channel 114, while a shaped arm 108 and a lower extension lip 138 extend perpendicularly from the middle wall 106 to define a second rod connector channel 116. In the preferred embodiment, the boundaries of the second rod connector channel 116 are defined by a hooked portion 136 of the shaped arm 108 and the lower extension lip 138. In the preferred embodiment, the swivel collet 122 is retained in the first rod connector channel 114. In some embodiments, the connector body 102 may also be formed with an angled surface edge portion 121 at the edges of the first side wall 104 and middle wall 106 that border the first rod connector channel 114.

Figure 7:
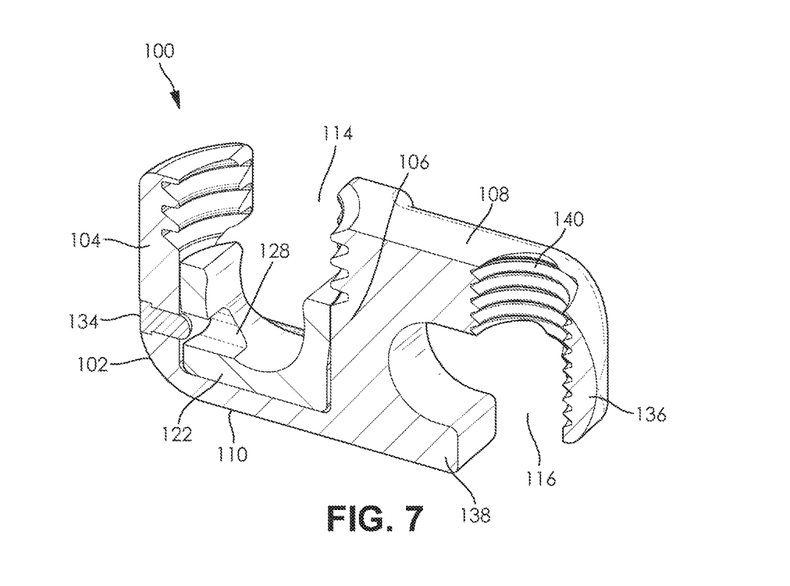
FIG. 7 is a cross-sectional view of a hooked open rod connector in accordance with an embodiment of the present invention.

FIG. 7 is a cross-sectional view of a hooked open rod connector in accordance with an embodiment of the present invention. In a preferred embodiment, the open rod connector 100 is comprised of a connector body 102, a swivel collet 122, and a collet pin 134. A side wall 104 and a middle wall 106 extend vertically from a base portion 110 of the connector body 102 to define a first rod connector channel 114, while a shaped arm 108 and a lower extension lip 138 extend perpendicularly from the middle wall 106 to define a second rod connector channel 116. In the preferred embodiment, the boundaries of the second rod connector channel 116 are defined by a hooked portion 136 of the shaped arm 108 and the lower extension lip 138. The second rod connector channel may also be formed with a threaded screw hole 140 that is formed in the shaped arm 108. In the preferred embodiment, the swivel collet 122 is retained in a collet-receiving depression formed in the first rod connector channel 114. The swivel collet 122 may be formed with a collet pin slot 128 that engages with the collet pin 134. The collet pin 134 is inserted into the connector body 102 at a collet pin outlet formed in the first side wall 104 of the connector body 102.

Figure 8:
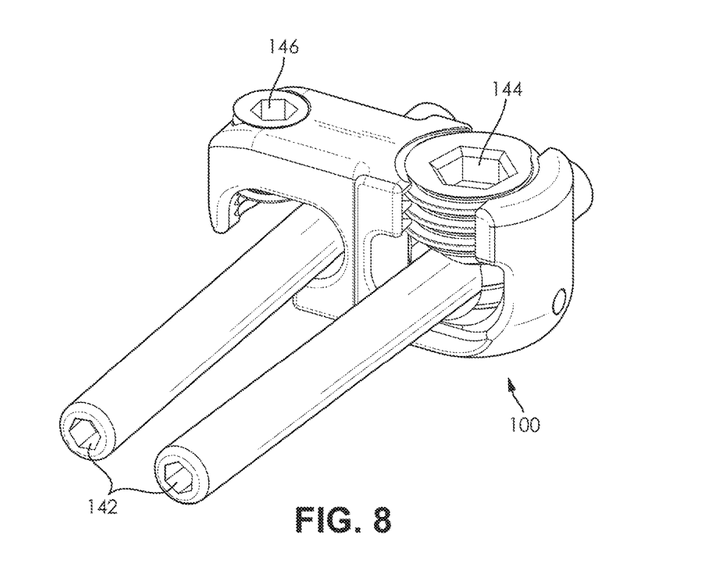
FIG. 8 is an illustration of a hooked open rod connector attached to two rods of a spinal fusion construct in accordance with an embodiment of the present invention.

FIG. 8 is an illustration of a hooked open rod connector attached to two rods of a spinal fusion construct in accordance with an embodiment of the present invention. In a preferred embodiment, the open rod connector is configured to connect together two pedicle rods to extend an existing spinal fusion construct. In the preferred embodiment of the hooked open rod connector, the hooked portion of the open rod connector 100 attaches over top of a pedicle rod and is secured to the pedicle rod 142 by a set screw 146 that engages with a threaded screw hole on the top of the shaped arm of the open rod connector 100. The U-shaped channel of the open rod connector 100 attaches from underneath the pedicle rod 142 and the pedicle rod is secured into the U-shaped channel with a set screw 144 that engages with internal threading at the top of the U-shaped channel.

Figure 9:
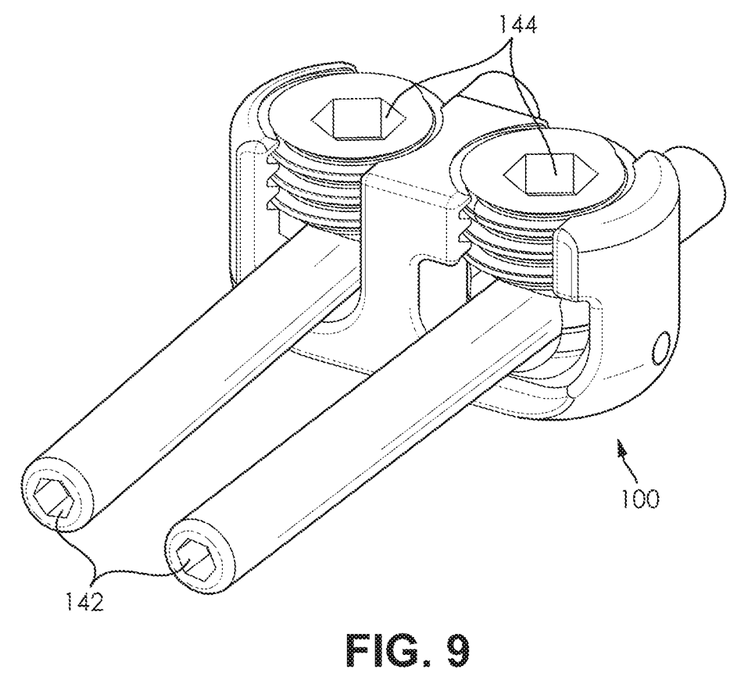
FIG. 9 is an illustration of a dual tulip open rod connector attached to two rods of a spinal fusion construct in accordance with an embodiment of the present invention.

FIG. 9 is an illustration of a dual tulip open rod connector attached to two rods of a spinal fusion construct in accordance with an embodiment of the present invention. In a preferred embodiment, the open rod connector is configured to connect together two pedicle rods to extend an existing spinal fusion construct. In the preferred embodiment of the dual tulip open rod connector, U-shaped channels of the open rod connector 100 attach from underneath the pedicle rods 142 and the pedicle rods 142 are secured in the U-shaped channel with set screws 144 that engage with internal threading at the top of the U-shaped channels.

It should be noted that the features illustrated in the drawings are not necessarily drawn to scale, and features of one embodiment may be employed with other embodiments as the skilled artisan would recognize, even if not explicitly stated herein. Descriptions of well-known components may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. An open rod connector for adding a rod to an existing fusion construct, said open rod connector comprising:
    a swivel collet;
    a collet pin; and
    a connector bracket having a W-shaped front profile, wherein a first trough of the W-shaped bracket defines a channel and a second trough of the W-shaped bracket defines a cradle dimensioned to receive the swivel collet that sits therein, wherein said cradle is a circular depression in a floor of said second trough,
    wherein said W-shaped bracket includes a plurality of walls, including left and right side walls and interior walls, each interior wall of the W-shaped bracket, above each trough, is threaded and configured to receive a set screw,
    wherein one of said side walls of the W-shaped bracket defines a collet pin outlet and a wall of the swivel collet defines a collet pin slot,
    wherein said swivel collet is configured to swivel inside said cradle when seated therein and swivel into a position in which said collet pin slot aligns with said collet pin outlet, and
    wherein said swivel collet rotates independently of the second trough when said collet pin is disposed within said collet pin slot.

2. The open rod connector of claim 1, wherein said first trough is configured to receive a first spinal fusion rod.

3. The open rod connector of claim 1, wherein said swivel collet defines a channel configured to receive a second spinal fusion rod.

4. The open rod connector of claim 1, wherein when said collet pin slot is aligned with said collet pin outlet, the aligned collet pin slot and collet pin outlet define an opening configured to receive said collet pin therethrough.

5. The open rod connector of claim 4, wherein said collet pin prevents said swivel collet from moving vertically within said cradle.

6. The open rod connector of claim 4, wherein said collet pin slot is configured to allow said swivel collet to rotate inside said cradle when said collet pin extends into said collet pin slot.

7. The open rod connector of claim 1, wherein the bottom of the swivel collet is dimensioned to fit in the cradle.

8. The open rod connector of claim 1, wherein the one of said side walls of the W-shaped bracket that defines the collet pin outlet includes a first angled surface edge portion and one of the interior walls, which defines the second trough, includes a second angled surface edge portion.

9. The open rod connector of claim 8, wherein said swivel collet defines a channel configured to receive a spinal fusion rod, and the first and second angled surface edge portions are configured to limit a rotation of the spinal fusion rod.

10. The open rod connector of claim 8, wherein at least one of a length of said collet pin slot and an angle of each of the first and second angled surfaces limits a rotation of the swivel collet to 60 degrees.

11. An open rod connector for adding a rod to an existing fusion construct, said open rod connector comprising:
    a swivel collet;
    a collet pin; and
    a connector bracket comprising a U-shaped connector portion and a hooked connector portion adjacent thereto;

wherein said U-shaped connector portion includes a trough and a wall on each opposite side of said trough, wherein interior sides of each wall, above the trough, are threaded and configured to receive a set screw, wherein the hooked connector portion comprises an arm with a hooking end segment and a threaded opening, said threaded opening comprising a proximal side and a distal side, wherein said distal side threading extends below said proximal side threading along an interior surface of said hooking end segment, wherein said trough defines a cradle dimensioned to receive the swivel collet, wherein a wall of the swivel collet defines a collet pin slot, and one wall of the U-shaped connector portion defines a collet pin outlet, wherein said swivel collet is configured to swivel inside said cradle when seated therein and swivel into a position in which said collet pin slot aligns with said collet pin outlet, and wherein said swivel collet rotates independently of said trough when said collet pin is disposed within said collet pin slot.

12. The open rod connector of claim 11, wherein said collet pin extends through said aligned collet pin slot and collet pin outlet thereby preventing said swivel collet from moving vertically within said cradle.

13. The open rod connector of claim 11, wherein said trough is configured to receive a first spinal fusion rod.

14. The open rod connector of claim 11, wherein said hooked connector portion defines a C-shaped opening configured to receive a second spinal fusion rod.

15. The open rod connector of claim 11, wherein said hooking end segment curves downward and extends below said threaded opening.

16. The open rod connector of claim 11, wherein each wall on each opposite side of said trough includes an angled surface edge portion.

17. The open rod connector of claim 11, wherein a width of the U-shaped connector portion is greater than a width of the hooked connector portion.

18. An open rod connector for adding a rod to an existing fusion construct, said open rod connector comprising:
 a swivel collet;
 a collet pin; and
 a connector bracket;
 wherein a first trough of the connector bracket defines a channel and a second trough of the connector bracket defines a cradle dimensioned to receive the swivel collet that sits therein, wherein said cradle is a circular depression in a floor of said second trough;
 wherein the connector bracket includes a plurality of walls, including left and right side walls and interior walls, each interior wall of the connector bracket, above each trough, is threaded and configured to receive a set screw;
 wherein one of said side walls of the connector bracket defines a collet pin outlet and a wall of the swivel collet defines a collet pin slot;
 wherein said swivel collet is configured to swivel inside said cradle when seated therein and swivel into a position in which said collet pin slot aligns with said collet pin outlet;
 wherein said swivel collet rotates independently of the second trough when said collet pin is disposed within said collet pin slot; and
 wherein the one of said side walls of the connector bracket that defines the collet pin outlet includes a first angled surface edge portion and one of the interior walls that defines the second trough includes a second angled surface edge portion.

19. The open rod connector of claim 18, wherein said swivel collet defines a channel configured to receive a spinal fusion rod, and the first and second angled surface edge portions are configured to limit a rotation of the spinal fusion rod.

20. The open rod connector of claim 19, wherein the first and second angled surface edge portions limit the rotation of the spinal fusion rod to 60 degrees.

* * * * *